United States Patent
Nakashima et al.

(10) Patent No.: US 6,333,436 B1
(45) Date of Patent: Dec. 25, 2001

(54) STYRENE DERIVATIVES

(75) Inventors: Matsuo Nakashima; Jun Hatakeyama; Jun Watanabe; Yuji Harada, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/688,365

(22) Filed: Oct. 12, 2000

(30) Foreign Application Priority Data

Oct. 13, 1999 (JP) .................................................. 11-291545

(51) Int. Cl.[7] ............................ C07C 41/22; C07C 25/28
(52) U.S. Cl. ........................... 568/630; 568/656; 570/127
(58) Field of Search ............................. 568/630, 656; 570/127

(56) References Cited

U.S. PATENT DOCUMENTS

| | | |
|---|---|---|
| 4,491,628 | 1/1985 | Ito et al. . |
| 5,843,624 | 12/1998 | Houlihan et al. . |
| 5,968,713 | 10/1999 | Nozaki et al. . |
| 5,998,099 | 12/1999 | Houlihan et al. . |
| 6,013,416 | 1/2000 | Nozaki et al. . |

FOREIGN PATENT DOCUMENTS

| | | |
|---|---|---|
| 63-27829 | 2/1988 | (JP) . |
| 2-27660 | 6/1990 | (JP) . |
| 9-73173 | 3/1997 | (JP) . |
| 9-230595 | 9/1997 | (JP) . |
| 09278688-A2 | * 10/1997 | (JP) . |
| 10-10739 | 1/1998 | (JP) . |
| WO 97/33198 | 9/1997 | (WO) . |

OTHER PUBLICATIONS

Albadri et al. Synthesis and reactivity of perfluorinated organometallic compounds. Nouv. J. Chim. (1982), 6 (11), 581–7. See abstract.*

Martin et al. Relative reactivities of acyclic, cyclic and spirobicyclic sulfuranes and sulfurane oxides. J. Amer. Chem. Soc. (1974), 96(10), 3155–68. See abstract.*

English Abstract for JP 63–27829.

English Abstract for JP 9–230595.

* cited by examiner

Primary Examiner—Johann Richter
Assistant Examiner—Sikarl A. Witherspoon
(74) Attorney, Agent, or Firm—Millen, White, Zelano & Branigan, P.C.

(57) ABSTRACT

Styrene derivatives of formula (1) are novel wherein $R^1$ is H, F, $C_{1-20}$ alkyl or fluorinated $C_{1-20}$ alkyl, $R^2$ in cis or trans conformation is F, $C_{1-20}$ alkyl or fluorinated $C_{1-20}$ alkyl, $R^3$ is a phenol protecting group, p, q and r are integers in the range of $0 \leq p < 5$, $0 \leq q < 5$, $0 < r < 5$, and $0 \leq p+q < 5$.

(1)

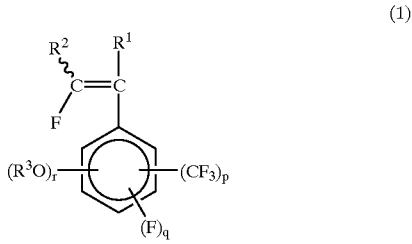

Polymers obtained by polymerizing the styrene derivatives are useful as the base polymer of resist compositions.

19 Claims, No Drawings

STYRENE DERIVATIVES

This invention relates to novel styrene derivatives which are useful monomers in preparing base polymers for use in chemically amplified resist compositions for microfabrication.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. In particular, the change-over from i-line (365 nm) to shorter wavelength KrF laser (248 nm) brought about a significant innovation, enabling mass-scale production of 0.18 micron rule devices. To the demand for a resist material with a higher resolution and sensitivity, acid-catalyzed chemical amplification positive working resist materials are effective as disclosed in U.S. Pat. No. 4,491,628 and U.S. Pat. No. 5,310,619 (JP-B 2-27660 and JP-A 63-27829). They now become predominant resist materials especially adapted for deep UV lithography.

Resist materials adapted for KrF excimer lasers enjoyed early use on the 0.3 micron process, went through the 0.25 micron rule, and currently entered the mass production phase on the 0.18 micron rule. Engineers have started investigation on the 0.15 micron rule, with the trend toward a finer pattern rule being accelerated. A wavelength change-over from KrF to shorter wavelength ArF laser (193 nm) is expected to enable miniaturization of the design rule to 0.13 µm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198. With respect to $F_2$ excimer laser (157 nm) which is expected to enable further miniaturization to 0.10 µm or less, more difficulty arises in insuring transparency because it was found that acrylic resins are not transmissive to light at all and those cycloolefin resins having carbonyl bonds have strong absorption.

SUMMARY OF THE INVENTION

An object of the invention is to provide a novel styrene derivative which is useful in the preparation of a base polymer for a chemical amplification resist composition having a high transmittance to vacuum ultraviolet radiation of up to 300 nm, especially $F_2$ excimer laser beam (157 nm), $Kr_2$ excimer laser beam (146 nm), KrAr excimer laser beam (134 nm) and $Ar_2$ excimer laser beam (126 nm).

It has been found that a novel styrene derivative of the following general formula (1) can be obtained by the method to be described later, and that using a resin based on a fluorinated polyhydroxystyrene obtained from the novel styrene derivative, a resist composition having transparency and alkali solubility is formulated.

As long as the inventor has confirmed, polyhydroxystyrene is somewhat improved in transmittance near 160 nm, but to an extent far below the practical level, and reducing carbonyl and carbon-to-carbon double bonds is essential for insuring a transmittance. However, phenols are good in etching resistance and alkali solubility, as compared with acrylic compounds. Further, halogen-substituted phenol polymers, and especially fluorine-substituted polymers obtained from the inventive styrene derivatives are improved in transmittance nearly to the practical level. The effect is obtained when the position of fluorine substitution is either on the benzene ring or on the backbone.

What becomes a problem as a result of wavelength reduction is a lowering of transparency, and in the case of a positive resist material, a negative working phenomenon that the exposed areas become insoluble as the dose of exposure is increased. Those portions which have turned negative are insoluble not only in alkali developers, but also in organic solvents such as acetone. This indicates that gel forms as a result of crosslinking of molecules together. Radical generation is probably one of the causes of the negative working phenomenon. As a result of wavelength reduction, the exposure energy is increased so that even C—C bonds and C—H bonds may be excited in the case of $F_2$ exposure (157 nm). As a result of excitation, radicals are generated with a possibility that molecules are bonded together. Moreover, since oxygen absorption is considerable in the VUV region, exposure is effected under the conditions that oxygen is purged, with an inert gas such as nitrogen or argon, to an oxygen concentration of 1 ppm or lower. Since oxygen is an effective radical trapping agent, this means that the radicals generated have a long lifetime and more crosslinking takes place. Since the energy of C—F bonds is greater than the energy of C—C bonds and C—H bonds, the C—F bonds are unsusceptible to scission upon exposure.

Therefore, fluorination of the backbone is effective to prevent crosslinking.

The invention provides a styrene derivative of the following general formula (1).

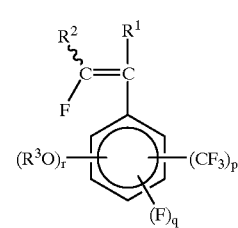

(1)

Herein the wavy line indicates either cis or trans conformation, $R^1$ is hydrogen, fluorine, an unsubstituted or fluoro-substituted, straight, branched or cyclic alkyl group of 1 to 20 carbon atoms, $R^2$ is fluorine or an unsubstituted or fluoro-substituted, straight, branched or cyclic alkyl group of 1 to 20 carbon atoms, $R^3$ is a phenol protecting group, p, q and r are integers in the range of $0 \leq p < 5$, $0 \leq q < 5$, $0 < r < 5$, and $0 p+q<5$.

DESCRIPTION OF THE PREFERRED EMBODIMENT

In formula (1) representative of the novel styrene derivative according to the invention, $R^1$ is hydrogen, fluorine, an unsubstituted or fluoro-substituted, straight, branched or cyclic alkyl group of 1 to 20 carbon atoms. Examples of the straight, branched or cyclic $C_{1-20}$ alkyl group represented by $R^1$ include methyl, ethyl, propyl, isopropyl, n-butyl, sec-butyl, tert-butyl, cyclopentyl, cyclohexyl, 2-ethylhexyl, and n-octyl. The alkyl groups of 1 to 4 carbon atoms are preferred, with methyl being most preferred. The fluorinated alkyl groups are the foregoing alkyl groups in which some or all of the hydrogen atoms are replaced by fluorine atoms, for example, trifluoromethyl, 2,2,2-trifluoroethyl, 3,3,3-trifluoropropyl, and 1,1,2,3,3,3-hexafluoropropyl. Preferably, $R^1$ is hydrogen, fluorine, methyl or trifluoromethyl.

$R^2$ is fluorine or an unsubstituted or fluoro-substituted, straight, branched or cyclic alkyl group of 1 to 20 carbon atoms. Examples of the straight, branched or cyclic $C_{1-20}$ alkyl group represented by $R^2$ include methyl, ethyl, propyl, isopropyl, n-butyl, sec-butyl, tert-butyl, cyclopentyl, cyclohexyl, 2-ethylhexyl, and n-octyl. The alkyl groups of 1 to 4 carbon atoms are preferred, with methyl being most preferred. The fluorinated alkyl groups are the foregoing alkyl groups in which some or all of the hydrogen atoms are replaced by fluorine atoms, for example, trifluoromnethyl, 2,2,2-trifluoroethyl, pentafluoroethyl, and nonafluorobutyl. Preferably, $R^2$ is fluorine, trifluoromethyl or pentafluoroethyl.

$R^3$ is a protective group on a phenol moiety, which is preferably selected from among methyl, vinyl, allyl, benzyl, and groups of the following general formulae (11), (12), (13), (14) and (15).

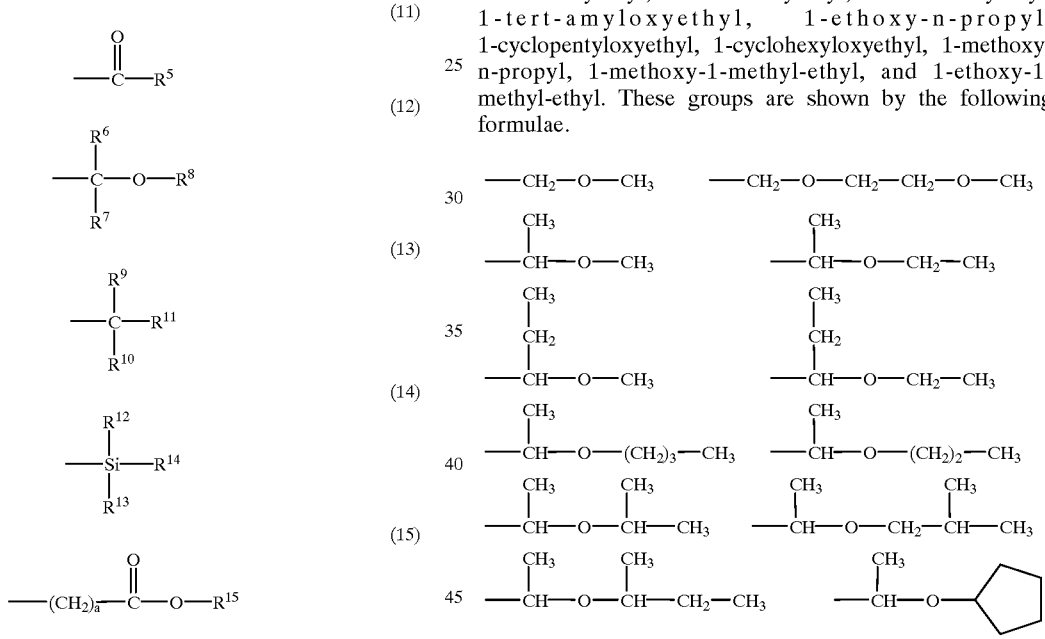

In formula (11), $R^5$ is a straight, branched or cyclic alkyl group of 1 to 20 carbon atoms. $R^6$ and $R^7$ each are hydrogen, a straight, branched or cyclic alkyl group of 1 to 20 carbon atoms which may contain a hetero atom, $R^8$ is a straight, branched or cyclic alkyl group of 1 to 20 carbon atoms which may contain a hetero atom, aryl, aralkyl or oxoalkyl group, and a pair of $R^6$ and $R^7$, a pair of $R^6$ and $R^8$, or a pair of $R^7$ and $R^8$, taken together, may form a cyclic structure of 3 to 12 carbon atoms. $R^9$, $R^{10}$ and $R^{11}$ each are a straight, branched or cyclic alkyl group of 1 to 20 carbon atoms which may contain a hetero atom, aryl, aralkyl or oxoalkyl group, and a pair of $R^9$ and $R^{10}$, a pair of $R^9$ and $R^{10}$, or a pair of $R^{10}$ and $R^{11}$, taken together, may form a cyclic structure of 3 to 12 carbon atoms. $R^{12}$, $R^{13}$ and $R^{14}$ each are a straight or branched alkyl group of 1 to 4 carbon atoms. $R^{15}$ is a straight, branched or cyclic alkyl group of 1 to 20 carbon atoms which may contain a hetero atom, aryl, aralkyl or oxoalkyl group, and "a" is an integer of 0 to 10.

Examples of the alkyl group represented by $R^5$ are the same as exemplified for $R^1$. Alkyl groups of 1 to 4 carbon atoms are preferred, with methyl being most preferred. Illustrative examples of the group of formula (11) are acetyl, propionyl, butyryl and isobutyryl.

In formula (12), examples of the alkyl group represented by $R^6$, $R^7$ and $R^8$ are the same as exemplified for $R^1$. Alkyl groups of 1 to 8 carbon atoms, especially 1 to 6 carbon atoms are preferred. These alkyl groups may contain a hetero atom such as oxygen, sulfur, nitrogen or fluorine. Examples are alkyl groups which are separated by an oxygen atom, sulfur atom or NH group. Also included are alkyl groups in which some or all of the hydrogen atoms are replaced by fluorine atoms.

A pair of $R^6$ and $R^7$, a pair of $R^6$ and $R^8$, or a pair of $R^7$ and $R^8$, taken together, may form a cyclic structure of 3 to 12 carbon atoms, especially 5 to 10 carbon atoms. Each of $R^6$, $R^7$ and $R^8$ is an alkylene group that forms a cyclic structure having the desired number of carbon atoms, when they form a ring.

Illustrative examples of the group of formula (12) are straight or branched acetal groups such as methoxymethyl, methoxyethoxymethyl, 1-methoxyethyl, 1-ethoxyethyl, 1-n-propoxyethyl, 1-isopropoxyethyl, 1-n-butoxyethyl, 1-isobutoxyethyl, 1-sec-butoxyethyl, 1-tert-butoxyethyl, 1-tert-amyloxyethyl, 1-ethoxy-n-propyl, 1-cyclopentyloxyethyl, 1-cyclohexyloxyethyl, 1-methoxy-n-propyl, 1-methoxy-1-methyl-ethyl, and 1-ethoxy-1-methyl-ethyl. These groups are shown by the following formulae.

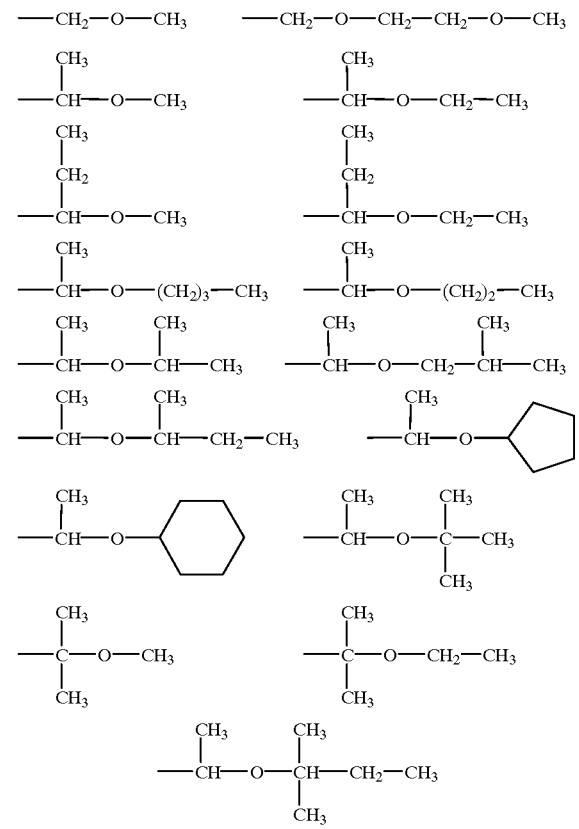

Of the groups represented by formula (12), cyclic groups are, for example, tetrahydrofuran-2-yl, 2-methyltetrahydrofuran-2-yl, tetrahydropyran-2-yl and 2-methyltetrahydropyran-2-yl. Of the groups represented by formula (12), ethoxyethyl, butoxyethyl, and ethoxypropyl are preferred.

In formula (13), examples of the alkyl group represented by $R^9$, $R^{10}$ and $R^{11}$ are the same as exemplified for $R^1$. Alkyl groups of 1 to 8 carbon atoms, especially 1 to 6 carbon atoms are preferred. These alkyl groups may contain a hetero atom such as oxygen, sulfur, nitrogen or fluorine. Examples are alkyl groups which are separated by an oxygen atom, sulfur atom or NH group. Also included are alkyl groups in which some or all of the hydrogen atoms are replaced by fluorine atoms.

A pair of $R^9$ and $R^{10}$, a pair of $R^9$ and $R^{11}$, or a pair of $R^{10}$ and $R^{11}$, taken together, may form a cyclic structure of 3 to 12 carbon atoms, especially 5 to 10 carbon atoms. Each of $R^9$, $R^{10}$ and $R^{11}$ is an alkylene group that forms a cyclic structure having the desired number of carbon atoms, when they form a ring.

Illustrative examples of the tertiary alkyl group of formula (13) include tert-butyl, triethylcarbyl, 1-ethylnorbornyl, 1-methylcyclohexyl, 1-ethylcyclopentyl, 2-(2-methyl) adamantyl, 2-(2-ethyl)adamantyl, and tert-amyl.

In formula (14), examples of the alkyl group represented by $R^{12}$, $R^{13}$ and $R^{14}$ are methyl, ethyl, propyl, isopropyl, n-butyl, sec-butyl, and tert-butyl. Illustrative examples of the group of formula (14) include trimethylsilyl, triethylsilyl and tert-butyldimethylsilyl.

In formula (15), examples of the alkyl group represented by $R^{15}$ are the same as exemplified for $R^1$. The hetero atoms which can be contained in these alkyl groups are as exemplified for $R^6$ to $R^{11}$. Illustrative examples of the group of formula (15) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl, 2-tetrahydrofuranyl-oxycarbonylmethyl, triethylcarbyloxycarbonylmethyl, 1-ethylnorbornyloxycarbonylmethyl, 1-methylcyclohexyloxy-carbonylmethyl, 1-ethylcyclohexyloxycarbonylmethyl, 1-methylcyclopentyloxycarbonylmethyl, 1-ethylcyclopentyl-oxycarbonylmethyl, 2-(2-methyl)adamantyloxycarbonylmethyl, 2-(2-ethyl)adamantyloxycarbonylmethyl, and tert-amyloxy-carbonylmethyl.

Also, $R^8$, $R^9$, $R^{10}$, $R^{11}$ and $R^{15}$ stand for substituted or unsubstituted aryl groups of 6 to 20 carbon atoms, for example, phenyl groups, p-methylphenyl, p-ethylphenyl, and alkoxy-substituted phenyl groups such as p-methoxyphenyl, aralkyl groups of 7 to 20 carbon atoms, such as benzyl and phenethyl. Also included are similar alkyl and other groups having an oxygen atom, similar alkyl and other groups in which a hydrogen atom attached to a carbon atom is replaced by a hydroxyl group, and similar alkyl and other groups in which two hydrogen atoms are replaced by an oxygen atom to form a carbonyl group, as shown below.

—(CH$_2$)$_4$—OH  —(CH$_2$)$_2$O(CH$_2$)$_3$CH$_3$

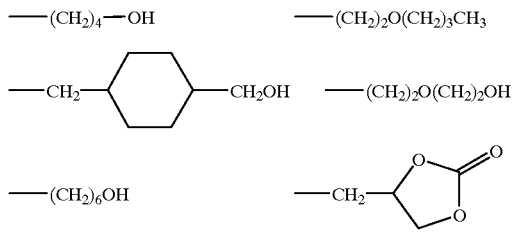

—(CH$_2$)$_6$OH

Also, $R^8$, $R^9$, $R^{10}$, $R^{11}$ and $R^{15}$ stand for oxoalkyl groups of 4 to 20 carbon atoms, for example, 3-oxoalkyl groups and groups as shown below.

Referring back to formula (1), p, q and r are integers in the range of $0\leq p<5$, $0\leq q<5$, $0<r<5$, and $0\leq p+q<5$. The preferred range is $q\geq 2$ and $r=1$.

Accordingly, the styrene derivative of the present invention is preferably of the following general formula (2), more preferably of the following general formula (3), and further preferably of the following general formula (4).

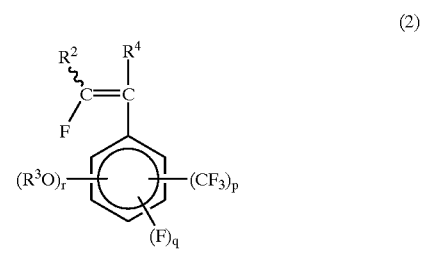

(2)

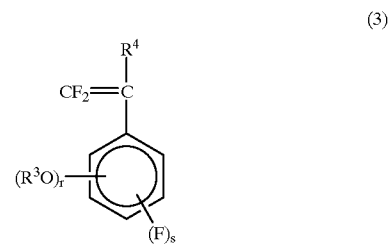

(3)

(4)

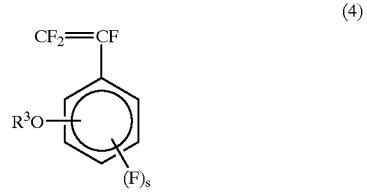

Herein, $R^4$ is hydrogen, fluorine, methyl or trifluoromethyl, $R^3$, p, q, r and the wavy line are as defined above, and s is an integer in the range of $0<s<5$.

Of the styrene derivatives, those having the $OR^3$ group at the para position are preferred. Accordingly, the styrene derivatives of the following general formula (5), especially the following general formulae (6) to (9) are preferable.

(5)

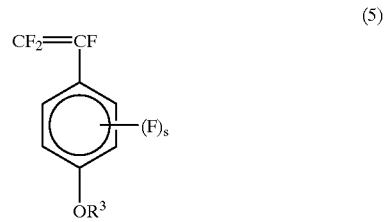

(6)

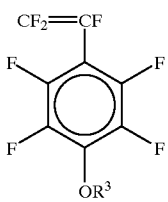

(7)

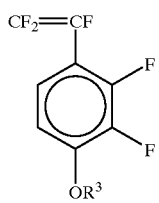

(8)

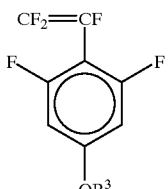

(9)

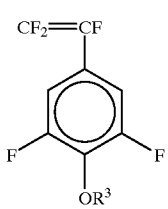

Herein R³ is as defined above.

Also preferred are those styrene derivatives having the OR³ group at the meta position represented by the following general formula (10).

(10)

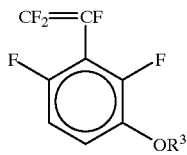

Herein R³ is as defined above.

The styrene derivative of the invention is generally prepared by cross coupling a benzene derivative of the following general formula (1a) with a vinyl derivative of the following general formula (1b).

(1a)

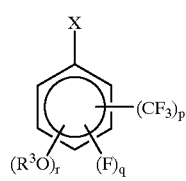

(1b)

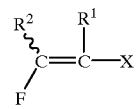

Herein, $R^1$, $R^2$, $R^3$, p, q, r and the wavy line are as defined above, and X is a halogen atom, i.e., fluorine, chlorine, bromine or iodine, and especially bromo or iodo.

In effecting the cross coupling, organometallic compounds are prepared from the compounds of formula (1a) or (1b), examples of the organometallic compounds including organic lithium compounds, organic magnesium compounds, organic zinc compound, organic copper compounds, organic titanium compounds, organic tin compounds and organic boron compounds. Transition metal catalysts such as palladium, nickel and copper catalysts must be used in the cross coupling. Exemplary palladium catalysts include zero-valent palladium compounds such as tetrakis(triphenylphosphine)-palladium(0) and di(1,2-bis(diphenylphosphino)-ethane)palladium(0), divalent palladium compounds such as palladium acetate, palladium chloride, and [1,1'-bis-(diphenylphosphino)ferrocene]palladium(II) chloride, complexes of the divalent palladium compounds with ligands, and combinations of the divalent palladium compounds with reducing agents.

Exemplary nickel catalysts include divalent nickel compounds such as (1,3-bis(diphenylphosphino)propane)nickel chloride (II), (1,2-bis(diphenylphosphino)ethane)nickel chloride (II), and bis(triphenylphosphine)nickel chloride (II), and zero-valent nickel compounds such as tetrakis-(triphenylphosphine)nickel(0).

Exemplary copper catalysts include monovalent copper salts such as copper (I) chloride, copper (I) bromide, copper (I) iodide, and copper (I) cyanide, divalent copper salts such as copper (II) chloride, copper (II) bromide, copper (II) iodide, copper (II) cyanide, and copper (II) acetate, and copper complexes such as dilithium tetracuprate.

Using the styrene derivative of the invention as a monomer, a polymer or high molecular weight compound is prepared. The polymer is generally prepared by mixing the monomer with a solvent, adding a catalyst thereto, and effecting polymerization reaction while heating or cooling the system if necessary. The polymerization reaction depends on the type of initiator or catalyst, trigger means (including light, heat, radiation and plasma), and polymerization conditions (including temperature, pressure, concentration, solvent, and additives). Commonly used for the polymerization of the styrene derivative of the invention are radical polymerization of triggering polymerization with radicals of α,α'-azobisisobutyronitrile (AIBN) or the like, and ion (anion) polymerization using catalysts such as alkyl lithium. Such polymerization may be effected in a conventional manner.

The polymer thus obtained is used as a base polymer in formulating a resist composition. The resist composition is generally formulated by adding an organic solvent and a photoacid generator to the polymer. If necessary, a crosslinker, basic compound, dissolution inhibitor and the like are added. The resist composition may be prepared in a conventional way.

The resist composition prepared using a polymer obtained by polymerizing the inventive styrene derivative is sensitive to high-energy radiation, has excellent sensitivity and resolution at a wavelength of up to 200 nm, especially up to 170 nm, and excellent plasma etching resistance. The styrene derivative of the invention is an advantageous raw material for a base polymer for formulating a resist composition having a low absorption at the exposure wavelength of a $F_2$ excimer laser. The resulting resist composition is ideal as a micropatterning material in VLSI fabrication since a finely defined pattern having sidewalls perpendicular to the substrate can easily be formed.

EXAMPLE

Examples of the invention are given below by way of illustration and not by way of limitation. AIBN denotes α,α'-azobisisobutyronitrile, and THF denotes tetrahydrofuran.

Example 1

Synthesis of 4-tert-butoxy-2,3-difluoro-α,β,β-trifluoro-styrene

A 1-liter reactor was charged with 31.2 g (0.10 mol) of 4-tert-butoxy-2,3-difluoro-1-iodobenzene and 100 ml of THF and heated at 60° C. To the reactor, 1.16 g (1 mmol) of tetrakis(triphenylphosphine)palladium(0) was added, then 300 ml of a THF solution of 1 M trifluorovinyl zinc iodide was added dropwise. After the completion of dropwise addition, the reaction solution was ripened for 30 minutes and poured into a saturated ammonium chloride aqueous solution. From the solution, a crude product was extracted with ethyl acetate in a conventional way. It was purified by silica gel chromatography, obtaining 21.5 g (yield 81%) the end product.

IR (ν): 2981, 1776, 1624, 1504, 1477, 1369, 1311, 1159, 1070, 1024, 883, 858 (cm$^{-1}$)

$^1$H-NMR: 1.40 ppm (9H, s) 6.85–6.95 ppm (1H, m) 7.03–7.12 ppm (1H, m)

Example 2

Synthesis of 4-tert-butoxy-2,6-difluoro-α,β,β-trifluoro-styrene

The end product was obtained as in Example 1 except that 4-tert-butoxy-2,6-difluoro-1-iodobenzene was used instead of the 4-tert-butoxy-2,3-difluoro-1-iodobenzene.

Example 3

Synthesis of 4-tert-butoxy-3,5-difluoro-α,β,β-trifluoro-styrene

The end product was obtained as in Example 1 except that 4-tert-butoxy-3,5-difluoro-1-iodobenzene was used instead of the 4-tert-butoxy-2,3-difluoro-1-iodobenzene.

Example 4

Synthesis of 4-tert-butoxy-2,3,5,6-tetrafluoro-α,β,β-trifluorostyrene

The end product was obtained as in Example 1 except that 4-tert-butoxy-2,3,5,6-tetrafluoro-1-iodobenzene was used instead of the 4-tert-butoxy-2,3-difluoro-1-iodobenzene.

Example 5

Synthesis of 3-tert-butoxy-2,6-difluoro-β,β-difluorostyrene

The end product was obtained as in Example 1 except that 3-tert-butoxy-2,6-difluoro-1-iodobenzene was used instead of the 4-tert-butoxy-2,3-difluoro-1-iodobenzene, and 2,2-difluorovinyl zinc chloride used instead of the trifluorovinyl zinc iodide.

Example 6

Synthesis of 4-acetoxy-2,3-difluoro-α,β,β-trifluorostyrene

The end product was obtained as in Example 1 except that 4-acetoxy-2,3-difluoro-1-iodobenzene was used instead of the 4-tert-butoxy-2,3-difluoro-1-iodobenzene.

Example 7

Synthesis of (E)-4-(1-ethoxyethyloxy)-2-fluoro-α,β-difluoro-β-trifluoromethylstyrene The end product was obtained as in Example 1 except that 4-(1-ethoxyethyloxy)-2-fluoro-1-iodobenzene was used instead of the 4-tert-butoxy-2,3-difluoro-1-iodobenzene, and (Z)-1,2-difluoro-2-trifluoromethylvinyl zinc iodide used instead of the trifluorovinyl zinc iodide.

Example 8

Synthesis of 4-tert-butoxy-3-fluoro-α,β,β-trifluorostyrene

The end product was obtained as in Example 1 except that 4-tert-butoxy-3-fluoro-1-iodobenzene was used instead of the 4-tert-butoxy-2,3-difluoro-1-iodobenzene.

Example 9

Synthesis of (Z)-3-methoxymethyloxy-4-fluoro-α,β-difluoro-β-trifluoromethylstyrene The end product was obtained as in Example 1 except that 3-methoxymethyloxy-4-fluoro-1-iodobenzene was used instead of the 4-tert-butoxy-2,3-difluoro-1-iodobenzene and (E)-1,2-difluoro-2-trifluoromethylvinyl zinc iodide used instead of the trifluorovinyl zinc iodide.

Example 10

Synthesis of 4-(2-tetrahydropyranyloxy)-2,3,5,6-tetrafluoro-α,β,β-trifluorostyrene The end product was obtained as in Example 1 except that 4-(2-tetrahydropyranyloxy)-2,3,5,6-tetrafluoro-1-iodobenzene was used instead of the 4-tert-butoxy-2,3-difluoro-1-iodobenzene.

Example 11

Synthesis of (E)-2-allyloxy-4-fluoro-α,β-difluoro-β-pentafluoroethylstyrene

The end product was obtained as in Example 1 except that 2-allyloxy-4-fluoro-1-iodobenzene was used instead of the 4-tert-butoxy-2,3-difluoro-1-iodobenzene, and (Z)-1,2-difluoro-2-pentafluoroethylvinyl zinc iodide used instead of the trifluorovinyl zinc iodide.

Example 12

Synthesis of (Z)-2-tert-butyldimethylsilyloxy-5-fluoro-α,β-difluoro-β-pentafluoroethylstyrene The end product was obtained as in Example 1 except that 2-tert-butyldimethylsilyloxy-5-fluoro-1-iodobenzene was used instead of the 4-tert-butoxy-2,3-difluoro-1-iodobenzene, and (E)-1,2-difluoro-2-pentafluoroethylvinyl zinc iodide used instead of the trifluorovinyl zinc iodide.

Example 13

Synthesis of 3-tert-butoxycarbonyloxy-2-fluoro-β,β-difluorostyrene

The end product was obtained as in Example 1 except that 3-tert-butoxycarbonyloxy-2-fluoro-1-iodobenzene was used instead of the 4-tert-butoxy-2,3-difluoro-1-iodobenzene, and 2,2-difluorovinyl zinc chloride used instead of the trifluorovinyl zinc iodide.

Example 14

Synthesis of 4-(1-ethylcyclopentyloxycarbonylmethyloxy)-2,6-difluoro-α,β,β-trifluorostyrene The end product was obtained as in Example 1 except that 4-(1-ethylcyclopentyloxycarbonylmethyloxy)-2,6-difluoro-1-iodobenzene was used instead of the 4-tert-butoxy-2,3-difluoro-1-iodobenzene.

Example 15

Synthesis of 2-vinyloxy-4,5,6-trifluoro-β,β-difluoro-α-trifluoromethylstyrene

The end product was obtained as in Example 1 except that 2-vinyloxy-4,5,6-trifluoro-1-iodobenzene was used instead of the 4-tert-butoxy-2,3-difluoro-1-iodobenzene, and 2,2-difluoro-1-trifluoromethylvinyl zinc iodide used instead of the trifluorovinyl zinc iodide.

Example 16

Synthesis of (E)-3-acetoxy-2,4,6-trifluoro-α,β-difluoro-β-n-butylstyrene

The end product was obtained as in Example 1 except that 3-acetoxy-2,4,6-trifluoro-1-iodobenzene was used instead of the 4-tert-butoxy-2,3-difluoro-1-iodobenzene, and (Z)-2-n-butyl-1,2-difluorovinyl zinc iodide used instead of the trifluorovinyl zinc iodide.

Example 17

Synthesis of 3-tert-butoxy-4,5,6-trifluoro-α,β,β-trifluoro-styrene

The end product was obtained as in Example 1 except that 3-tert-butoxy-4,5,6-trifluoro-1-iodobenzene was used instead of the 4-tert-butoxy-2,3-difluoro-1-iodobenzene.

Example 18

Synthesis of 3-acetoxy-4-trifluoromethyl-α,β,β-trifluorostyrene

The end product was obtained as in Example 1 except that 3-acetoxy-4-trifluoromethyl-1-iodobenzene was used instead of the 4-tert-butoxy-2,3-difluoro-1-iodobenzene.

Example 19

Synthesis of (Z)-2-tert-butoxy-6-fluoro-α,β-difluoro-β-trifluoromethylstyrene

The end product was obtained as in Example 1 except that 2-tert-butoxy-6-fluoro-1-iodobenzene was used instead of the 4-tert-butoxy-2,3-difluoro-1-iodobenzene, and (E)-1,2-difluoro-2-trifluoromethylvinyl zinc iodide used instead of the trifluorovinyl zinc iodide.

Example 20

Synthesis of 3-benzyloxy-6-fluoro-α,β,β-trifluorostyrene

The end product was obtained as in Example 1 except that 3-benzyloxy-6-fluoro-1-iodobenzene was used instead of the 4-tert-butoxy-2,3-difluoro-1-iodobenzene.

Reference Example 1

Synthesis of poly(2,3-difluoro-4-hydroxy-α,β,β-trifluoro-styrene)

In a 2-liter flask, 120 g of 4-tert-butoxy-2,3-difluoro-α,β,β-trifluorostyrene was dissolved in 560 ml of toluene. After oxygen was fully purged out of the system, 5.5 g of initiator AIBN was admitted. The flask was heated at 60° C., at which polymerization reaction was effected for 24 hours. In order to work up the polymer, the reaction mixture was poured into a 3/2 mixture of hexane and ether whereupon the polymer precipitated. The polymer was separated and dried, obtaining 110 g of a white polymer. The polymer was transferred to a 2-liter flask and dissolved in acetone to form a 15% solution. After the solution was heated at 60° C., 46 ml of 12N hydrochloric acid was slowly added dropwise, and deblocking reaction was effected for 7 hours. Pyridine, 66 g, was added to the reaction solution, which was concentrated and poured into liters of pure water, whereupon the polymer precipitated. The procedure of dissolving the collected polymer in acetone and pouring into 5 liters of pure water for precipitation was repeated twice. The polymer was separated and dried. There was obtained 81 g of a white polymer. This polymer was found to have a weight average molecular weight (Mw) of 13,000 g/mol as measured by the light scattering method and a dispersity (Mw/Mn) of 1.65 as determined from the GPC elution curve.

Reference Example 2

Synthesis of poly(3,5-difluoro-4-hydroxy-α,β,β-trifluorostyrene)

In a 2-liter flask, 120 g of 4-tert-butoxy-3,5-difluoro-α,β,β-trifluorostyrene was dissolved in 560 ml of toluene. After oxygen was fully purged out of the system, 5.5 g of initiator AIBN was admitted. The flask was heated at 60° C., at which polymerization reaction was effected for 24 hours. In order to work up the polymer, the reaction mixture was poured into a 3/2 mixture of hexane and ether whereupon the polymer precipitated. The polymer was separated and dried, obtaining 110 g of a white polymer. The polymer was transferred to a 2-liter flask and dissolved in acetone to form a 15% solution. After the solution was heated at 60° C., 46 ml of 12N hydrochloric acid was slowly added dropwise, and deblocking reaction was effected for 7 hours. Pyridine, 66 g, was added to the reaction solution, which was concentrated and poured into liters of pure water, whereupon the polymer precipitated. The procedure of dissolving the collected polymer in acetone and pouring into 5 liters of pure water for precipitation was repeated twice. The polymer was separated and dried. There was obtained 81 g of a white polymer. This polymer was found to have a weight average molecular weight (Mw) of 14,000 g/mol as measured by the light scattering method and a dispersity (Mw/Mn) of 1.75 as determined from the GPC elution curve.

Japanese Patent Application No. 11-291545 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A styrene derivative of the following general formula (1):

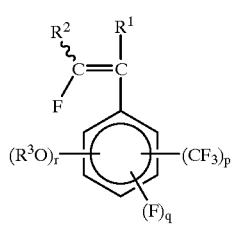

(1)

wherein the wavy line indicates cis or trans conformation, $R^1$ is hydrogen, fluorine, an unsubstituted or fluoro-substituted, straight, branched or cyclic alkyl group of 1 to 20 carbon atoms, $R^2$ is fluorine or an unsubstituted or fluoro-substituted, straight, branched or cyclic alkyl group of 1 to 20 carbon atoms, $R^3$ is a phenol protecting group, and p, q and r are integers in the range of $0 \leq p < 5$, $0 \leq q < 5$, $0 < r < 5$, and $0 < p+q < 5$.

2. The styrene derivative of claim 1 which is represented by the following formula (2):

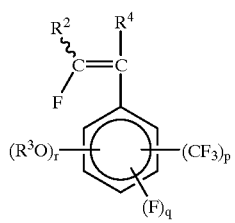

(2)

wherein $R^4$ is hydrogen, fluorine, methyl or trifluoromethyl, $R^2$, $R^3$, p, q, r and the wavy line are as defined above.

3. The styrene derivative of claim 2 which is represented by the following formula (3):

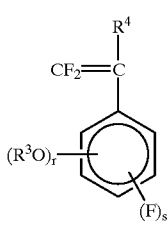

(3)

wherein $R^3$, $R^4$ and r are as defined above and s is an integer in the range of $0 < s < 5$.

4. The styrene derivative of claim 3 which is represented by the following formula (4):

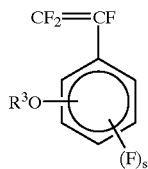

(4)

wherein $R^3$ and s as defined above.

5. The styrene derivative of claim 4 which is represented by the following formula (5):

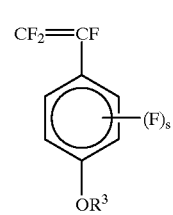

(5)

wherein $R^3$ and s are as defined above.

6. The styrene derivative of claim 5 which is represented by the following formula (6):

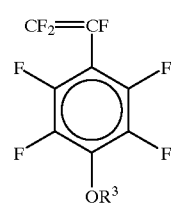

(6)

wherein $R^3$ is as defined above.

7. The styrene derivative of claim 5 which is represented by the following formula (7):

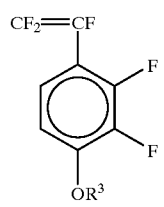

(7)

wherein $R^3$ is as defined above.

8. The styrene derivative of claim 5 which is represented by the following formula (8):

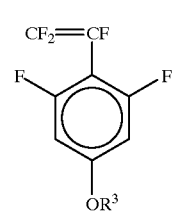

(8)

wherein $R^3$ is as defined above.

9. The styrene derivative of claim 5 which is represented by the following formula (9):

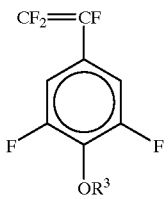
(9)

wherein $R^3$ is as defined above.

10. The styrene derivative of claim 4 which is represented by the following formula (10):

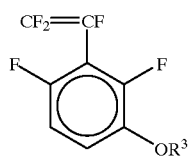
(10)

wherein $R^3$ is as defined above.

11. The styrene derivative of claim 1 wherein $R^3$ is selected from the class consisting of methyl, vinyl, allyl, benzyl, and groups of the following general formulae (11), (12), (13), (14) and (15):

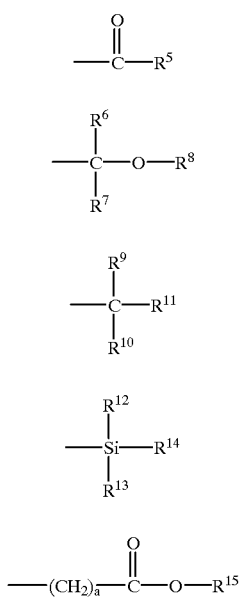

wherein $R^5$ is a straight, branched or cyclic alkyl group of 1 to 20 carbon atoms, $R^6$ and $R^7$ each are hydrogen, a straight, branched or cyclic alkyl group of 1 to 20 carbon atoms which may contain a hetero atom, $R^8$ is a straight, branched or cyclic alkyl group of 1 to 20 carbon atoms which may contain a hetero atom, aryl, aralkyl or oxoalkyl group, and a pair of $R^6$ and $R^7$, a pair of $R^6$ and $R^8$, or a pair of $R^7$ and $R^8$, taken together, may form a cyclic structure of 3 to 12 carbon atoms, $R^9$, $R^{10}$ and $R^{11}$ each are a straight, branched or cyclic alkyl group of 1 to 20 carbon atoms which may contain a hetero atom, aryl, aralkyl or oxoalkyl group, and a pair of $R^9$ and $R^{10}$, a pair of $R^9$ and $R^{11}$, or a pair of $R^{10}$ and $R^{11}$, taken together, may form a cyclic structure of 3 to 12 carbon atoms, $R^{12}$, $R^{13}$ and $R^{14}$ each are a straight or branched alkyl group of 1 to 4 carbon atoms, $R^{15}$ is a straight, branched or cyclic alkyl group of 1 to 20 carbon atoms which may contain a hetero atom, aryl, aralkyl or oxoalkyl group, and "a" is an integer of 0 to 10.

12. A styrene derivative of claim 1, wherein $R^1$ is an alkyl group of 1–4 carbon atoms.

13. A styrene derivative of claim 1, wherein $R^1$ is a methyl group.

14. A styrene derivative of claim 1, wherein $R^1$ is hydrogen, fluorine, methyl, or trifluoromethyl.

15. A styrene derivative of claim 1, wherein $R^2$ is an alkyl group of 1–4 carbon atoms.

16. A styrene derivative of claim 1, wherein $R^2$ is a methyl group.

17. A styrene derivative of claim 1, wherein $R^2$ is fluorine, trifluoromethyl or pentafluoroethyl.

18. A styrene derivative of claim 1, wherein $2 \leq q < 5$, and $r=2$.

19. A styrene derivative of the following formula (3):

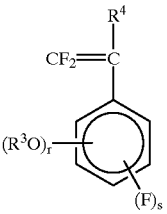
(3)

wherein:

$R^3$ is a phenol protecting group;

$R^4$ is hydrogen, fluorine, methyl or trifluoromethyl; and r and s are integers in the range of $0 < r < 5$ and $0 < s < 5$.

* * * * *